United States Patent [19]
Smith et al.

[11] Patent Number: 5,979,228
[45] Date of Patent: Nov. 9, 1999

[54] METHOD FOR DETERMINATION OF $^{18}O/^{16}O$ AND $^{2}H/^{1}H$ RATIOS AND $^{3}H$ (TRITIUM) CONCENTRATIONS OF XYLEM WATERS AND SUBSURFACE WATERS USING TIME SERIES SAMPLING

[76] Inventors: Brian Smith; Leticia Menchaca, both of 1126 Delaware St., Berkeley, Calif. 94702

[21] Appl. No.: 08/995,106

[22] Filed: Dec. 19, 1997

Related U.S. Application Data

[60] Provisional application No. 60/036,709, Dec. 20, 1996.

[51] Int. Cl.$^6$ .......................... G01N 37/00; G01N 33/18
[52] U.S. Cl. .......................... 73/53.01; 73/61.41
[58] Field of Search .................. 73/53.01, 61.41, 73/61.43

[56] References Cited

PUBLICATIONS

G. L. Stewart, et al., Tritium in Pine Trees From Selected Locations in the United States, Including Areas Nuclear Facilities, *Geological Survey Research*, U.S. Geol. Survey Prof. Paper, 800–B, pp. B265–B271 (1972).

R. L. Wershaw, et al., Hydrogen Isotopic Fractionation of Water Passing Through Trees, *Advances in Organic Geochemistry*, vol. 32, pp. 55–67 (1966).

R. Gonfiantini, et al, Oxygen Isotopic Composition of Water in Leaves, Laboratorio Di Geologia Nucleare, University of Pisa, Cnen, Italy.

G. Dongmann, et al., On the Enrichment of $H_2{}^{18}O$ in the Leaves of Transpiring Plants, *Rad. Environm. Biophys.*, 11, 41–52 (1974).

Tritium in the Physical and Biological Sciences II, Symposium, International Atomic Energy Agency, Vienna, selected pages, (1962).

Isotopic Variations in Meteoric Waters, *Science*, vol. 133, pp. 1702–1703 (May 26, 1961).

*Primary Examiner*—Daniel S. Larkin
*Attorney, Agent, or Firm*—Hana Verny

[57] ABSTRACT

A method for determination of $^{18}O/^{16}O$ and $^{2}H/^{1}H$ ratios and $^{3}H$ concentrations of xylem and subsurface waters using time series sampling, insulating sampling chambers, and combined $^{18}O/^{16}O$, $^{2}H/^{1}H$ and $^{3}H$ concentration data on transpired water. The method involves collecting water samples transpired from living plants and correcting the measured isotopic compositions of oxygen ($^{18}O/^{16}O$) and hydrogen ($^{2}H/^{1}H$ and/or $^{3}H$ concentrations) to account for evaporative isotopic fractionation in the leafy material of the plant.

14 Claims, 1 Drawing Sheet

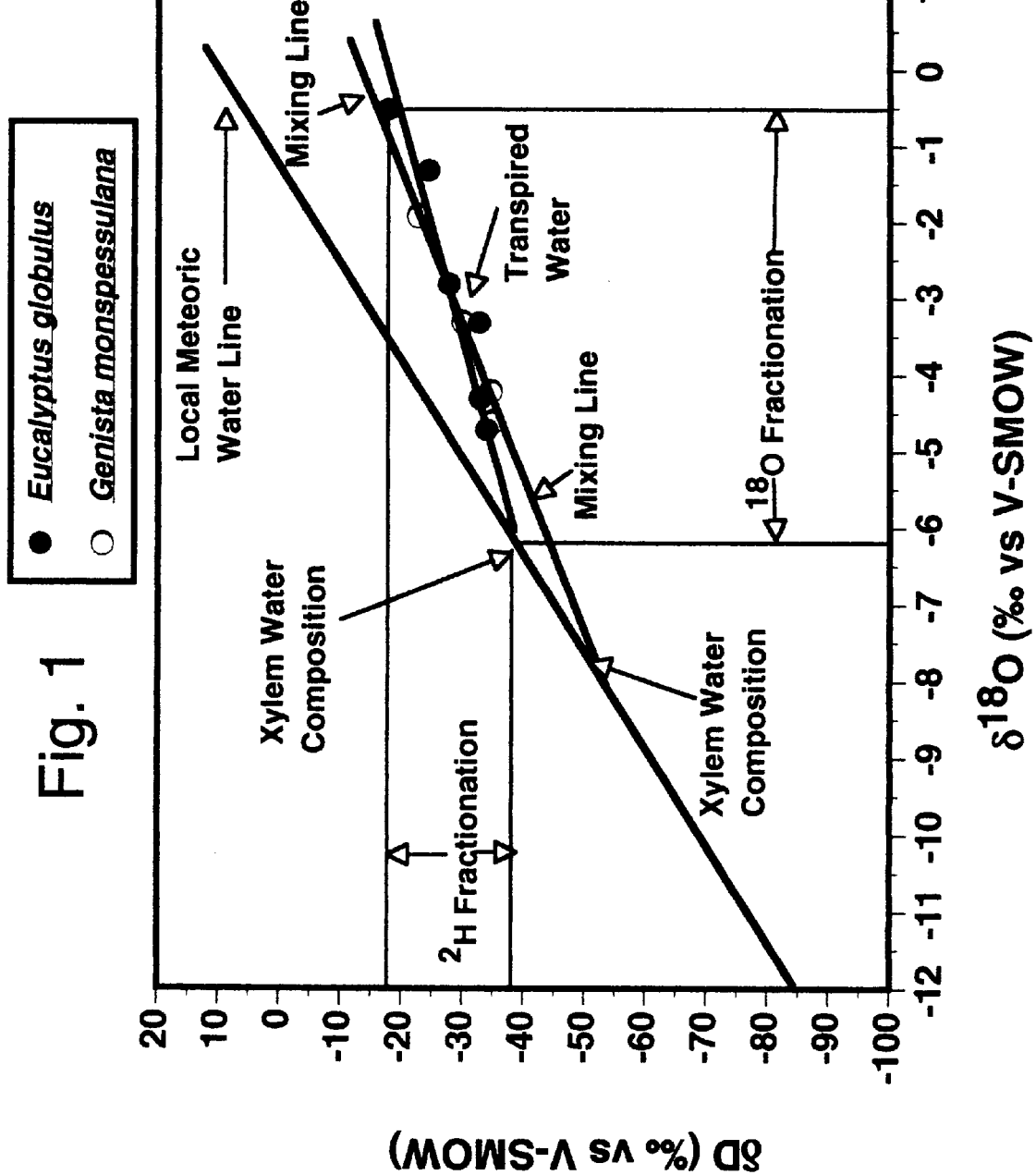

METHOD FOR DETERMINATION OF $^{18}O/^{16}O$ AND $^2H/^1H$ RATIOS AND $^3H$ (TRITIUM) CONCENTRATIONS OF XYLEM WATERS AND SUBSURFACE WATERS USING TIME SERIES SAMPLING

This application is based on the Provisional Application Ser. No. 60/036,709, filed on Dec. 20, 1996.

This invention was made with government support under the Management and Operations Contract #DE-ACO3-76SF0098, awarded by the Department of Energy.

BACKGROUND OF THE INVENTION

1. Field of Invention

This invention concerns a method for determination of $^{18}O/^{16}O$ and $^2H/^1H$ ratios and $^3H$ concentrations of xylem and subsurface waters using time series sampling, insulating sampling chambers, and combined $^{18}O/^{16}O$, $^2H/^1H$ and $^3H$ concentration data on transpired water. In particular, the method involves collecting water samples transpired from living plants and correcting the measured isotopic compositions of oxygen ($^{18}O/^{16}O$) and hydrogen ($^2H/^1H$ and/or $^3H$ concentrations) to account for evaporative isotopic fractionation in the leafy material of the plant.

2. Background Art and Related Art Disclosures

Traditional approaches to obtain samples of soil water or shallow groundwater for stable isotopic ($^{18}O/^{16}O$ or $^2H/^1H$) or tritium ($^3H$) analyses have focused on intrusive sampling methods, including drilling wells, using hydropunches, digging trenches, or otherwise excavating the earth and obtaining water samples through pumping, using vacuum lysimeters, or removing the water from soils using physical methods such as compression, cryogenic trapping, or centrifugation, or chemical methods such as azeotropic distillation. Similarly, traditional approaches to obtain samples of plant xylem waters for isotopic characterization involve destructive sampling of woody plant material.

Many researchers have obtained water samples from various plant tissues for purposes of studying the isotopic compositions of the waters, as summarized in *Stable Isotopes and Plant Carbon-Water Relations,* 510 (1993), Academic Press.

*Advances in Organic Geochemistry,* 55–67 (1966), Pergamon Press, describes the use of plant xylem water to determine the stable isotopic compositions of hydrogen and oxygen in shallow environmental waters and shows that plant xylem water is not isotopically fractionated during root uptake or transport to the plant leaf as xylem water.

*Isotopes and Radiation in Soil-Plant Nutrition Studies,* IAEA:410–415 (1965) shows that bulk leaf water becomes enriched in the heavy isotopes of hydrogen and oxygen due to evaporative fractionation. Because the amount of heavy sotope enrichment in water extracted from the leafy tissues of plants depends on such factors as transpiration rate, humidity, wind velocity, plant species, and local soil conditions, it is difficult to accurately predict the degree of heavy isotope enrichment in the leafy material of a given plant.

It would, therefore, be advantageous to have available a method for determination of a degree of heavy isotope enrichment in the leafy material of plants.

*Stable Isotopes in Plant Carbon-Water Relations:* 529–540 (1993) presents theoretical aspects of stable isotope relationships in plant leaf tissue and demonstrates the difficulty in accurately modeling or predicting the stable isotopic compositions of leaf water due to compartmentalization, and perhaps to species-dominated and capacitance-related effects.

*Stable Isotopes in Plant Carbon-Water Relations, Physical Ecology Series, Eds.* Ehleringer et al., Academic Press, Inc., pages 71–90 (1993) discusses the theory and modeling of stable isotope relations in transpired water and shows that precise application of the existing models require stable isotopic analysis of plant stem water and atmospheric water vapor.

Transpired waters, collected and analyzed for the stable isotopic compositions of hydrogen and oxygen provided similar results. As described in *Radiation and Environmental Biophysics,* 11:41–52 (1974), transpired waters were shown to be isotopically disturbed, with non-equilibrium enrichments in the heavy isotopes of hydrogen and oxygen due to evaporation during water residence in the plant leaf.

Because mass dependent fractionation of light isotopes depends only on the relative masses of the fractionating isotopes, $^3H$ fractionation in the leafy materials of plants is expected to be 50% stronger than $^2H$ fractionation under equilibrium conditions, and 33%–50% stronger than $^2H$ fractionation under disequilibrium conditions, as reported in *Tritium in the Physical and Biological Sciences,* 1, IAEA Report No. ST1/PUB/39: 161 (1962).

Environmental Tritium in Trees, IAEA-WM-232/44: 405–418 (1979) showed that one can determine the distribution of $^3H$ in shallow subsurface waters by conducting $^3H$ activity measurements of plant xylem waters.

To accurately determine the stable isotopic compositions of hydrogen and oxygen and the tritium concentrations of soil waters and shallow groundwaters using analytical data for transpired waters, it is necessary to determine the amount of evaporative fractionation that has occurred during water residence in the plant leaf. However, a method to do so is currently not available. Until the current invention, therefore, lack of knowledge regarding the degree to which tritium concentrations are disturbed during evaporation has made it impossible to accurately estimate tritium concentrations in subsurface waters from transpired water data.

It would be, thus, highly desirable to provide a sampling approach, analytical strategy, and data interpretation technique that would allow the determination of the amount of hydrogen and oxygen isotope fractionation in transpired water samples, and to use this information to determine the amount of evaporative tritium fractionation in those same transpired waters. This would allow the quantitative determination of the stable isotopic compositions and tritium activities of waters being used by the plant, whether those waters are from the saturated zone (shallow groundwaters) or the unsaturated zone (shallow soil waters).

It is, therefore, the primary object of the current invention to provide a method of sampling transpired waters, an analytical approach, and a data interpretation technique that would allow quantification of stable isotopic compositions and tritium activities of plant xylem waters and isotopically equivalent soil waters and/or shallow groundwaters being used by the plant.

SUMMARY

One aspect of the current invention concerns a method for determination of $^{18}O/^{16}O$ and $^2H/^1H$ ratios and $^3H$ concentrations of xylem and subsurface waters using time series sampling, insulating sampling chambers, and combined $^{18}O/^{16}O$, $^2H/^1H$, and $^3H$ concentration data on transpired water.

Another aspect of the current invention is a method for collecting water samples transpired from living plants and correcting the measured isotopic compositions of oxygen ($^{18}O/^{16}O$) and hydrogen ($^{2}H/^{1}H$ and/or $^{3}H$ concentrations) to account for evaporative isotopic fractionation in the leafy material of the plant.

Still another aspect of the current invention is a method of collecting transpired water containing any dissolved constituents, alone or in combination with cryogenic, chemical, or other water trapping approaches.

Another aspect of the current invention is a method for determination of the stable isotopic compositions and tritium activities of plant xylem waters by analyzing samples of transpired water collected from living plants.

Still yet another aspect of the current invention is a method for determining the amount of evaporative enrichment in $^{18}O$, $^{2}H$, and/or $^{3}H$ in transpired waters using insulating sampling chambers and time series sampling methods.

Still another aspect of the current invention is a method for investigation and detection of the stable isotopic compositions and tritium concentrations of soil waters and/or shallow groundwaters taken up by plants, using insulating sampling chambers and time series sampling.

Yet another aspect of the current invention is a method for determination of the amount of evaporative fractionation of hydrogen and oxygen isotopes in the leaves of plants using transpired water samples.

Yet another aspect of the current invention is a method illustrated in FIG. 1 useful for the determination of the stable isotopic composition of plant xylem water, using transpired waters as samples.

Yet another aspect of the current invention is a method illustrated in FIG. 1 useful for the determination of the amount of $^{18}O$- and $^{2}H$-fractionation of plant transpired waters, collected individually or in time-series.

Still another aspect of the current invention is a method for the arithmetic determination of the amount of evaporative tritium enrichment in transpired water samples which allows the correction of measured tritium concentrations or activities to reflect those of the plant xylem water, and isotopically equivalent shallow subsurface waters being used by the plant, prior to evaporation.

Yet another aspect of the invention is the use of insulating sampling chambers to promote transpiration from the leafy portions of plants.

DEFINITIONS

As used herein:

"Insulating sampling chamber" means and includes any relatively impermeable enclosure such as a bag, tube, bottle, jar, box, or other enclosure that, when tightly sealed to a portion of a plant to enclose living leafy material, generates an internally water saturated condition, promotes transpiration and precludes evaporation of the water sample to the environment.

"Fractionation" means a change in the relative abundances of the isotopes of oxygen and/or hydrogen in waters due to physical processes such as evaporation or condensation.

"Groundwaters" means subsurface waters residing in the saturated zone, without regard for origin.

"Isotopic fractionation" means the same as "Fractionation".

"Leaf" means that green, photosynthesizing portion of a living plant, including a leaf, needle, frond, blade, or other similar branch termination.

"Leaf water" means water residing within the leafy portion of a plant.

"Leafy material" means an aggregation of leaves.

"Plant" means any living tree, bush, shrub, vine, grass, fern, cactus, bamboo, or other macroscopic photosynthesizing organism with a root structure that penetrates to any depth into the soil.

"Shallow subsurface waters" means soil waters, perched waters, groundwaters, or waters from any other source that are sufficiently close to the earth's surface to be used by the root systems of macroscopic plants for metabolism and growth.

"Soil waters" means subsurface waters residing in the unsaturated (vadose) zone, above the local water table, including any ephemeral or local perched waters above the water table, without regard to origin.

"Time series" means collected serially in a regular or irregular time sequence, such as daily for two to five days.

"Transpired" means escaping from the leafy portion of a plant, without regard to mechanism or condition.

"Transpired water" means water that has escaped from the leafy portion of a plant, without regard to mechanism or condition.

"Xylem" means the woody material of plants, including tissues from the root, trunk, limb, branch, twig, or bark.

"Xylem water" means the aqueous component of plant xylem.

"Evaporative enrichment" means the relative enrichment of the heavy isotopes of hydrogen ($^{2}H$ or $^{3}H$) and/or oxygen ($^{18}O$) in waters that have been partially evaporated, relative to the light isotopes ($^{1}H$ and/or $^{16}O$) in those same waters.

BRIEF DESCRIPTION OF DRAWINGS

FIG. 1 is a graphical illustration of methods of the invention for determination of the stable isotopic composition of plant xylem water and amount of $^{18}O$ and $^{2}H$ fractionation of plant transpired waters.

DETAILED DESCRIPTION OF THE INVENTION

The current invention is directed to the fields of and is useful for environmental or ecological assessments or monitoring, health risk assessment, public exposure, water management, forestry and agricultural studies, forensic investigations, engineering studies, botanical investigations, or other similar work in which it is advantageous to know the isotopic compositions of oxygen, particularly its $^{18}O/^{16}O$ ratio and/or hydrogen $^{2}H/^{1}H$ ratio and/or $^{3}H$ concentration in plant xylem waters or in shallow subsurface waters, including soil waters, perched waters, and groundwaters.

The invention concerns a method for determination of $^{18}O/^{16}O$ and $^{2}H/^{1}H$ ratios and $^{3}H$ concentrations of xylem and subsurface waters using time series sampling, insulating sampling chambers, and combined $^{18}O/^{16}O$, $^{2}H/^{1}H$, and $^{3}H$ concentration data on transpired water. The method comprises collecting water samples transpired from living plants and correcting the measured isotopic compositions of oxygen $^{18}O/^{16}O$ and hydrogen $^{2}H/^{1}H$ and/or $^{3}H$ concentrations, to account for evaporative isotopic fractionation in the leafy material of the plant. The step of correcting the measured isotopic compositions of transpired waters is necessary because the concentrations of $^{18}O$, $^{2}H$, and $^{3}H$ are too high due to the earlier preferential loss of the light isotopes $^{16}O$ and $^{1}H$ during evaporation in the plant leaf. Such heavy isotope enrichments cause changes in the $^{18}O/^{16}O$ and $^2H/^1H$ ratios and $^3H$ concentrations of transpired waters, so these parameters must be corrected downward to represent xylem water/shallow subsurface water compositions.

In order to prevent and/or inhibit evaporation during sample collection, the method utilizes insulating sampling chambers. Samples are collected in time-series to identify temporal trends in the isotopic compositions, and to allow graphical or numerical analysis for the amount of isotopic fractionation for purposes of characterizing the isotopic compositions of plant xylem waters or shallow subsurface waters in environmental, water management, public health, radiological, hydrologic, engineering, ecological, forensic, agricultural, or other similar investigations or monitoring programs. Collected water samples including any dissolved constituents transpired by living plants are investigated and the stable isotopic compositions and/or tritium concentrations or any other constituents of the plant xylem waters or of subsurface waters being used by the plant root systems are determined.

The invention further provides methods for sampling, analytical design, data analysis, data interpretation, and their use for determination of stable isotopic compositions and tritium concentrations of xylem waters and shallow subsurface waters from transpired water samples.

In practice, the current method comprises obtaining transpired waters from living plants and correcting the measured stable isotopic ratios and/or tritium concentrations to reflect the compositions of the xylem waters within the plants and isotopically equivalent subsurface waters used by the plants, without the need for excavation, drilling, destructive sampling, or other environmental intrusions. The transpired water samples are collected from insulating sampling chambers tightly secured to the limbs or leafy areas of living plants. By entirely emptying the sampling chamber each day during the sampling period of time lasting from several hours to several weeks, preferably for two to five days, the water samples are investigated for proportions of unfractionated xylem water and fractionated leaf water. The method for sampling transpired water is described in greater detail in Example 1.

The transpired water samples are transferred to an analytical laboratory equipped with a gas-source mass spectrometer and the samples are analyzed for their hydrogen isotopic ration ($^2H/^1H$) and oxygen isotopic ratio ($^{18}O/^{16}O$). The data are expressed in generally acceptable units traditionally used for such analyses, i.e. as $\delta D$ and $\delta^{18}O$ values, in per/mil (%), that is in parts-per-thousand relative to publicly available Vienna-Standard Mean Ocean Water (V-SMOW). The water sample size varies from about 1 ml to about 40 ml depending on the concentration of the isotopes, but it is preferred that for this analysis at least 10 milliliters of water is collected. Larger samples are utilized when the duplicate analysis is desirable or required, for example, for quality assurance. Smaller samples can be utilized for oxygen and hydrogen isotope ratio analysis, but may require alternative methods of sample preparation prior to analysis. Any analytical method used should be as accurate and precise as possible, with uncertainties of less than ±2% for $\delta D$ values and less that ±0.2% for $\delta^{18}O$ values.

In addition, one or more of the transpired water samples from each plant is also submitted to an analytical laboratory for determination of $^3H$ (tritium) concentration, using equipment such as a scintillation counter to determine the amount of radioactivity in the sample that is attributed to the presence of $^3H$. Data are typically expressed in units, such as picoCuries/L or picoCuries/ml, or by using any other suitable measurement units of tritium activity expression. For samples with relatively high tritium concentrations, 10 mls may be sufficient for determination of tritium activity. Larger samples may be required if tritium concentrations are lower, to allow larger sample for counting, or to permit preconcentration or pretreatment, such as substitution on a hydrogen-rich organic molecule, such as benzene, prior to analysis. As with the stable isotopes, it is important to obtain high quality information on tritium activity, with larger samples generally providing more accurate and precise analytical information.

Once the stable isotopic and tritium activity data are obtained, a traditional Meteoric Water Line diagram, such as seen in FIG. 1 is constructed. The Meteoric Water Line data and diagram are described in Science, 133:1702–1703 (1961). In this type of diagram, $\delta D$ values are plotted on the Y-axis (vertical axis) and $\delta^{18}O$ values are plotted on the X-axis (horizontal axis) in units of per mil (%) relative to V-SMOW. The scales represented on the X- and Y-axes should encompass all of the data for the transpired water samples for any plant such that all of the data appear on the plot.

On the same graph, the local (if known) or Global Meteoric Water Line is plotted, as shown on FIG. 1. This Meteoric Water Line is important, because most xylem waters and shallow subsurface waters that are utilized by plants have stable isotopic compositions that fall on this line. Soil waters in arid areas, however, may have stable isotopic compositions that fall to the right of the Meteoric Water Line due to evaporation prior to infiltration. In arid areas, therefore, it is important to obtain sufficient stable isotopic data for local soil waters to allow construction of a local soil water line, which would be plotted on the diagram, as is shown in FIG. 1.

When the $\delta D$ and $\delta^{18}O$ values for the transpired waters for any plant are plotted on the Meteoric Water Line diagram, the data are found to form linear arrays with slopes approximately half as steep as the slope of the Meteoric Water Line, as shown in FIG. 1 for two plants from Berkeley, Ca. These linear arrays are interpreted to present mixing lines and are a graphical representation of fact that the transpired water samples, when collected in time series, are mixtures composed of two isotopically distinctive endmembers. One of the endmembers is xylem water, which is isotopically equivalent to the subsurface water being used by the plant. The other endmember is leaf water, which has been enriched $^2H$ and $^{18}O$ by being subjected to evaporation in the plant leaf. The xylem water endmember, as stated above, is expected to have a stable isotopic composition that lies somewhere along the Meteoric Water Line and somewhere along the projection of the transpired water mixing line.

The development and testing of the invention reached the following conclusions:

The stable isotopic composition of the plant xylem water can be inferred to lie at the intersection of Meteoric Water Line and the transpired water mixing line on a diagram such as FIG. 1, when transpired water samples are collected in time series and analyzed for $\delta D$ and $\delta^{18}O$ values;

The amount of evaporative $^2H$- and $^{18}O$-enrichment can be determined for any of the transpired water samples, by comparing the measured $\delta D$ and $\delta^{18}O$ values for the transpired waters with the inferred stable isotopic composition of the plant xylem water;

The amount of evaporative $^3H$ fractionation in any of the transpired water samples can be estimated, by multiplying the observed $^2$H-enrichment for that sample by a factor that accounts for the relative mass differences between the hydrogen isotopes;

That similar values of evaporative enrichment in transpired waters can be predicted for many varieties of plants and trees in a given area, such that this approach could be used to calibrate a given species in a particular climate for the amount of evaporative enrichment typically observed in transpired water samples. Once a species and climate have been calibrated in this fashion, stable isotopic compositions and $^3$H activities can be estimated for xylem water and shallow subsurface waters based on analyses of transpired water samples, without the need for time-series sampling.

The current invention thus allows the quantitative determination of the amount of evaporative oxygen and hydrogen isotopic fractionation that has occurred in the transpired water, and permits meaningful estimations of the stable isotopic compositions and tritium concentrations of xylem water and of shallow subsurface waters in vegetated areas.

The invention offers many advantages over previously known and available methods for determining the stable isotopic compositions and tritium concentrations of xylem waters and shallow subsurface waters. The current methods differ substantially from all references cited in the Background section in that samples are taken sequentially, in time series, that an insulating sampling chamber that envelops a plant limb is employed, and that evaporative oxygen and hydrogen isotopic fractionations are determined using graphical or numerical methods, and that stable isotope compositions of xylem waters are determined by correcting for the $^{18}$O and $^2$H fractionation, and tritium ($^3$H) concentrations in the transpired waters are corrected to xylem water values using the deuterium fractionation multiplied by a mass-dependent scaling factor. Using the current methods, stable isotopic compositions and tritium concentrations of plant xylem water and shallow subsurface water(s) are determined based on analytical results of transpired waters.

The method comprises the following steps:

(a) An insulating sampling chamber is tightly secured around a portion of a living plant in order to collect transpired water and any dissolved constituents in the water. This step may include combination with cryogenic, chemical, or other water trapping approaches. In alternative, this step includes collection of samples of soil waters and/or shallow groundwaters taken up by plants, using insulating sampling chambers and time series sampling.

(b) Water is collected and removed in predetermined intervals, preferably once or twice daily for periods of time as needed to obtain as accurate determination of the slope of the mixing line as possible. Typically, such period will be two-five days, but may be from several hours to several days or even weeks when plant transpiration rates are low. To this end, it is desirable to collect the first sample as soon as enough water (approximately 10–20 ml) has accumulated in the chamber to allow stable isotope and tritium activity measurements to be performed.

(c) Determination of the stable isotopic compositions and tritium activities of plant xylem waters by analyzing samples of transpired water collected from living plants.

(d) Plotting of stable isotopic data and a local Meteoric Water Line or Global Meteoric Water Line on a Cartesian graph of $\delta$D vs $\delta^{18}$O and a mixing line of best fit and constructing a mixing line of best fit through the transpired water data.

(e) Determining the amount of evaporative fractionation of $^2$H and $^{18}$O and the stable isotopic composition of xylem water or subsurface water from the point of intersection of the mixing line and the local or Global Meteoric Water Line using transpired water samples.

(f) Calculating the amount of evaporative tritium enrichment by inference from the amount of deuterium fractionation per transpired water sample and the well known mass dependence of light isotopic fractionation. This last step involves the arithmetic determination of the amount of evaporative tritium enrichment in transpired water samples, allowing the correction of measured tritium concentrations or activities to reflect those of the plant xylem water, or isotopically equivalent shallow subsurface waters being used by the plant prior to evaporation.

The method of the invention is illustrated in FIG. 1. FIG. 1 shows the construction of mixing lines between fractionated leaf water and unfractionated plant xylem water from stable isotopic compositions of transpired waters collected in time series using insulating sampling chambers. Lines of best fit are calculated for each data array using well known statistical methods such as the least squares method, which can be performed on a scientific calculator. Alternatively, the best fit line can be drawn through the transpired water data, as shown in FIG. 1. The regular linear progressions from the first collected samples (the most $^{18}$O- and $^2$H-rich samples, i.e., the samples plotting the highest and farthest to the right on a diagram like FIG. 1) to progressively lower $\delta^{18}$O and $\delta$D are taken to indicate that the isotopic data form mixing lines between isotopically fractionated leaf water endmembers and isotopically unfractionated xylem water endmembers for each plant. The fact that the line segments have slopes of between ~2.5 and ~5.0 imply that the physical processes causing the isotopic fractionations in the leaf water endmembers are dominated by evaporation.

FIG. 1 also shows the graphical solution for the stable isotopic compositions of xylem waters and isotopically equivalent subsurface waters being used by a plant, based on the stable isotopic analysis of transpired waters. In addition, FIG. 1 shows how to graphically solve for the amount of $^{18}$O-, and $^2$H-fractionation in water samples transpired by plants, based on the stable isotopic analysis and tritium analysis of transpired waters.

As illustrated on FIG. 1, the data for successive transpired water samples from *Eucalyptus globulus* and *Genista monspessulana* progressively approach the Meteoric Water Line along chords with slopes of ~3.85 and ~4.50, respectively. This shifting of stable isotopic compositions is anticipated because the air inside a sealed collection bag almost immediately becomes water saturated, precluding further evaporation. The first collected sample contains a significant amount of water that has experienced some evaporation in the plant leaf. Each successive daily sample contains a smaller component of evaporated leaf water and a larger component of unfractionated leaf water that continues to arrive from the body of the plant.

The transpired water data arrays on FIG. 1 are interpreted to be linear mixing trends with evaporated leaf water and unevaporated xylem water as the endmembers. Although the proportions of the two endmembers cannot be determined from this treatment, the intersections of the mixing lines and the local or Global Meteoric Water Line gives the actual stable isotopic compositions of hydrogen and oxygen in the unevaporated xylem water endmember. This isotopic composition accurately represents the water currently used by the plant root system. For the Berkeley Laboratory samples, the projected stable isotopic compositions of soil water ($\delta^{18}$O=−7.2‰ and $\delta$D=−58‰, from the *Genista monspessu-*

*lana* data) and for groundwater ($\delta^{18}O=-6.2\%$ and $\delta D=-40\%$, from the *Eucalyptus globulus* data) are within the ranges recorded for subsurface waters at this site.

In greater detail, in practicing the invention, first one or more plants are selected for investigation. A suitably insulating sampling chamber is securely attached over a limb of the tree or the bush or any other protuberance with leafy materials. In general, the chamber should be somewhat transparent to sun light and the chamber may or may not be equipped with a closeable opening such as a tube or cap for the purposes of evacuating the collected water. After 24 hours, or another suitable period, the transpired water is wholly removed from the chamber to the extent practicable and the chamber is resealed. This process is repeated for at least two, and preferably three to five sampling intervals, where one sampling interval is typically one day, producing a series of samples containing differing amounts of xylem water and leaf water. Typically, sampling for more than six days has not added useful information and may begin to injure or kill the portion of the plant enclosed in the sampling chamber. However, periods longer than six days of sampling may be required for plants with extremely low transpiration rates. In these instances, care is taken to avoid any injury to the plant by, for example, limiting the contact between the plant and the collecting bag.

The transpired water samples are analyzed for the stable isotopic compositions of hydrogen ($^2H/^1H$, expressed as $\delta D$ vs V-SMOW) and oxygen ($^{18}O/^{16}O$, expressed as $\delta^{18}O$ vs V-SMOW) using general mass spectrometric methods, with or without any sample pretreatment, such as transpired water distillation to remove plant resins or other impurities. Tritium analyses may also be conducted on the water samples, using generally known and used laboratory methods, such as scintillation counting, with or without pretreatment such as mentioned above, i.e. distillation to remove plant resins or other impurities that may adversely affect the tritium analysis.

The stable isotopic data are then plotted on a Cartesian graph of $\delta D$ vs $\delta^{18}O$ a traditional Meteoric Water Line diagram, and a line of best fit, hereinafter "mixing line" is constructed through the transpired water data. A local Meteoric Water Line is also plotted on the same graph, or is substituted by the Global Meteoric Water Line when stable isotope data for local meteoric waters are not available. The equation for the Global Meteoric Water Line is $\delta D=(8\times \delta^{18}O)+10$, as reported in *Science*, 133: 1702–1703 (1961). The stable isotopic composition of xylem water, which is isotopically equivalent to the subsurface water being used by the plant, is determined from the point of intersection of the mixing line and the local or Global Meteoric Water Line, as seen in FIG. 1. The same graph is also used to determine the amount of evaporative fractionation of $^2H$ and $^{18}O$ in any of the transpired water samples, relative to the pre-evaporation isotopic compositions. This step is performed graphically, by determining the difference in $\delta D$ or $\delta^{18}O$ between the first-collected sample, for example, and the projected isotopic composition of the unfractionated xylem water endmember, as illustrated in FIG. 1. Alternatively, this step is performed arithmetically, by subtracting the $\delta D$ (or $\delta^{18}O$) value of the first-collected sample from the projected composition of the unfractionated xylem water endmember. Once the amount of deuterium fractionation is known for any of the transpired water samples, the amount of evaporative tritium enrichment is inferred from the well known mass dependence of light isotopic fractionation. This is accomplished by multiplying the deuterium fractionation by a factor between 1.33 and 1.50, to account for the stronger mass dependent fractionation of tritium.

One advantage of the current invention is its practicality. The ability to infer the isotopic compositions and/or tritium concentrations of plant xylem waters without the need for destructive sampling of the plant eliminates the sample preparation steps required to separate xylem waters from solid plant materials and makes the method of the invention very undemanding and practical.

The extraction of waters from plants is typically accomplished by approaches such as heating coupled with cryogenic trapping or azeotropic distillation with an organic solvent such as toluene, hexane, ether, etc., with significant safety and health hazards, requirements for highly skilled laboratory workers, and hazardous waste generation. The method is simpler than previously available approaches, requires only moderate energy and is thus less demanding on energy supplies and workers time, and is generally less damaging to plants, safer to humans, and less expensive.

Another advantage of the current invention is that it generates no mixed or hazardous waste. In areas of high tritium concentration, azeotropic distillation of xylem waters or leaf waters with a solvent such as toluene might generate mixed both hazardous waste, due to ignitability, and/or radioactive wastes, which are extremely expensive and difficult to manage and dispose. The methods of the current invention might generate low level radioactive waste in the form of tritiated water, but no mixed wastes are generated.

Another advantage of this invention is the ability to determine the isotopic compositions of oxygen and hydrogen in shallow, subsurface waters without the need for drilling wells, installing lysimeters, excavating trenches, operating a hydropunch, or employing other invasive methods of collecting subsurface water samples.

The methods of this invention are safer for workers, more protective of shallow groundwaters, more protective of surface waters and the environment, less expensive, simpler, require less equipment, are less socially and physically disruptive, and require considerably less training than traditional methods.

Another advantage of the current invention is the ability to accurately determine stable isotopic compositions and tritium concentrations in subsurface waters in localities that are environmentally and/or socially sensitive, such as wetlands, old growth forests, parks, schools, botanical gardens, wilderness areas, or other properties where road construction, drilling activities, and potential environmental contamination or other disruptions may preclude the use of traditional approaches.

Another advantage of the current invention is the greatly reduced costs of obtaining quantitative information regarding the stable isotopic compositions and/or tritium concentrations of xylem waters or shallow subsurface waters. In particular, the current invention allows many more observations to be made for a given investment of time and financial resources. This, in turn, allows characterization or monitoring programs or other investigations to be carried out at larger scales and/or in finer detail than traditional approaches such as drilling or otherwise excavating the land. In this regard, the current invention is particularly suited to large scale surveys of tritium distribution in soil waters and shallow groundwaters, for purposes of land use planning, public health risk assessment, or other similar purposes, especially in the vicinity of active or decommissioned nuclear reactors, nuclear weapons production facilities, waste treatment/storage/disposal sites, medical research laboratories, and other facilities that have released, continue to release, or have the potential to release tritium to the environment.

Another advantage of the current invention is its potential use in some types of characterization investigations or monitoring programs that have not been performed using traditional approaches due to high costs or logistical difficulties, such as areas that are inaccessible due to high relief, remoteness, or other factors.

Another advantage of the current invention is its potential use by citizen's groups, regulators, concerned neighbors, or any other member of the government or public for purposes of characterization and/or monitoring of stable isotopic compositions and/or tritium concentrations in xylem waters and/or shallow subsurface waters in soils or underground aquifers. The use of the current invention in this capacity may promote trust between agencies and facilities that release tritium to the environment and their local citizenry and neighbors, by giving citizens a cost-effective approach for carrying out their own stable isotope or tritium characterization and monitoring programs.

The invention is described and illustrated in great detail in examples.

Utility

The current invention is useful for the determination of the stable isotopic compositions and/or tritium concentrations of plant xylem waters and shallow, subsurface waters being used by plants in all macroscopically vegetated areas, or areas capable of supporting macroscopic vegetation, with or without irrigation or other plant husbandry. The methods of the current invention could be used in environmental, ecological, radiological, engineering, biological, water management, forensic, agricultural, botanical, or other similar work, either in the laboratory or in field investigations. The methods of the current invention may be useful in the above types of investigations at any scale, but are especially suited to large scale investigations, reconnaissance studies, or detailed studies requiring large numbers of observations.

In addition, the sampling methods of the current invention can be carried out safely by relatively unskilled/untrained labor, with suitable professional environmental support in the project design, analytical, and interpretive stages of an investigation or monitoring program.

The current invention can be applied to macroscopic vegetation in any area of the earth with ambient surface temperatures greater than freezing (0° C.) and offers distinct advantages over intrusive sampling methods, especially in areas that are remote, environmentally sensitive, protected, inaccessible, or otherwise unsuited for traditional invasive methods of subsurface water sample collection.

This invention is especially suited to the determination of stable isotopic compositions of xylem waters and shallow subsurface waters in investigations where it is desirable to obtain information about the source(s) of the subsurface water(s). For example, shallow zones of mixing between seawater and groundwater might be discerned. In another application, surveys could be conducted to determine the locations of leaking pipes or other municipal or facility waters supply lines, based on stable isotopic differences between the delivered water and ambient soil water or shallow groundwater. In yet another application, the methods of the current invention could be used to map the distribution of shallow subsurface waters of a given stable isotopic composition.

EXAMPLE 1

Method of Sampling Transpired Waters

This example illustrates the method of sampling transpired waters.

The method includes sampling of transpired waters comprising differing proportions of unfractionated xylem water and fractionated leaf water by securing an insulating sampling chambers over a portion of a plant, for the purpose of determining the stable isotopic compositions of hydrogen ($^2H/^1H$, expressed as $\delta D$ in % vs V-SMOW), oxygen ($^{18}O/^{16}O$, expressed as $\delta^{18}O$ in % vs V-SMOW), and $^3H$ concentration (expressed as tritium activity in pCi/Liter or pCi/ml) in the soil water or shallow groundwater being used by the plant.

Nearly transparent, colorless 10-gallon plastic bags were secured over low-hanging limbs of a mature Eucalyptus tree (*Eucalyptus globulus*) and a mature French Broom bush (*Genista monspessulana*) at the Ernest Orlando Lawrence Berkeley National Laboratory. Two rubber bands were placed approximately 4 cm apart near the neck of the bag to isolate the interior of the bag from the environment, to induce water saturated conditions within the chamber, and to preclude evaporation of collected transpired water to the environment. Transpired waters (10 to 200 ml) were nearly completely (>95%) drained from the bags each day for a period of 4–6 days. The bags were carefully resealed after each sampling to maintain water saturated conditions within the sampling chambers. The bags were removed after the final day of sampling to minimize damage to the plants.

The transpired water samples were placed in labeled, 40 ml glass containers with Teflon septa to preclude any further evaporation prior to isotopic analysis. No additional preservation or pretreatment method was required.

EXAMPLE 2

Graphical Determination of Mixing Lines

This example illustrates the procedure for obtaining the required stable isotopic data for the transpired water samples.

First, the transpired water samples were transferred to an analytical laboratory equipped with a gas-source mass spectrometer, where they were analyzed for stable isotopic ratios of hydrogen ($^2H/^1H$) and oxygen ($^{18}O/^{16}O$). The hydrogen isotope compositions were determined on hydrogen gas prepared from the samples by reduction over zinc at 400° C. In alternative, reduction over hot uranium or other similar preparation are used. The oxygen isotope rations were determined on $CO_2$ equilibrated overnight with the water samples at 25° C. Then, the $^2H/^1H$ and $^{18}O/^{16}O$ ratios were expressed as $\delta D$ and $\delta^{18}O$ values in per mil (parts-per-thousand) differences from the stable isotopic composition of V-SMOW (Vienna-Standard Mean Ocean Water).

EXAMPLE 3

Graphical Methods for Determining the Stable Isotopic Composition

This example illustrates the construction of a traditional Meteoric Water Line Diagram, the plotting of a local or Global Meteoric Water Line on the diagram, the plotting of $\delta D$ and $\delta^{18}O$ values for transpired waters on such a diagram, and the construction of mixing lines through the stable isotopic data for transpired waters.

First, a standard Meteoric Water Line Diagram was constructed. On this diagram, $\delta D$ values were plotted on the Y-axis (vertical axis) and $\delta^{18}O$ values on the X-axis (horizontal axis) in units of per mil (%), relative to V-SMOW, from the values obtained in Example 2, using the procedure and graph seen in FIG. 1. On the same graph, as seen in FIG. 1 the local meteoric water line for the Berkeley site, which was determined to be identical to the Global Meteoric Water Line was plotted. In the absence of availability of such local data, the Global Meteoric Water Line seen in FIG. 1 was plotted with no negative effects. The easiest way to plot this Global Meteoric Water Line was to construct a line with a slope of 8.0 that intercepts a point at ($\delta^{18}O=0$, $\delta D=10$).

Next, the $\delta D$ and $\delta^{18}O$ values which were obtained for the transpired water samples from the French Broom and Eucalyptus at Berkeley Lab were plotted into the same diagram. These values are seen in Table 1, below.

TABLE 1

Stable Isotopic Compositions of Transpired Water From French Broom (*Genista monspessulana*) and Eucalyptus (*Eucalyptus globulus*)

| Sample | Species | Day | $\delta^{18}O$ | $\delta D$ (%) |
|---|---|---|---|---|
| E1 | Eucalyptus globulus | 1 | −0.5 | −17.9 |
| E2 | Eucalyptus globulus | 2 | −1.3 | −24.5 |
| E3 | Eucalyptus globulus | 3 | −2.8 | −27.9 |
| E4 | Eucalyptus globulus | 4 | −3.3 | −32.9 |
| E5 | Eucalyptus globulus | 5 | −4.3 | −33.0 |
| E6 | Eucalyptus globulus | 6 | −4.6 | −35.0 |
| FB1 | Genista monspessulana | 1 | −1.9 | −22.8 |
| FB2 | Genista monspessulana | 2 | −3.3 | −30.2 |
| FB3 | Genista monspessulana | 3 | −4.2 | −34.9 |
| FB4 | Genista monspessulana | 4 | −4.6 | −35.0 |

The data for *Eucalyptus globulus* seen in Table 1, were plotted into and are seen as filled circles in the Meteoric Water Line diagram seen in FIG. 1. In FIG. 1, these data are seen as a linear array that lies to the right of, and has a slope shallower than the local meteoric water line. The $\delta D$ and $\delta^{18}O$ values obtained for transpired water samples from French Broom *Genista monspessulana*, seen as unfilled circles, were also plotted on the same Meteoric Water Line diagram as shown in FIG. 1. These data were also observed to form a linear array with a slope slightly steeper than that of the Eucalyptus data array.

Lines of best fit, which are labeled "Mixing Line" in FIG. 1, were then visually drawn through each data array and were extended to intersect the local meteoric water line. The equations for these lines were determined using the least squares method on a scientific calculator. The first-collected transpired water samples for each plant were found to lie the farthest to the right of the local meteoric water line, indicating that they contain the largest components of evaporated leaf water. Successive samples for each plant were found to be closer to the local meteoric water line because they contained progressively larger components of unevaporated xylem water.

This was also discerned from Table 1, above, where $\delta D$ and $\delta^{18}O$ values for each plant were seen to become more negative from the first sample to the sixth sample, for Eucalyptus and from the first sample to the fourth sample for French Broom.

EXAMPLE 4

Graphical Method for Determining the Amount of $^2H$, $^3H$ and $^{18}O$ Fractionation This example illustrates the graphical method for determining the amount of $^2H$, $^3H$, and $^{18}O$ fractionation in transpired water samples collected in time series from insulating sampling chambers.

The magnitude of the evaporative enrichment in deuterium (or $^{18}O$) is determined by comparing the $\delta D$- or $\delta^{18}O$-value of the first collected (or any other) sample to the projected composition of the unfractionated xylem water, as determined in Example 3. When the magnitude of deuterium fractionation has been determined, the amount of evaporative enrichment for tritium can be calculated, based on the well known mass dependence of light isotope fractionation. The relative tritium-hydrogen and deuterium-hydrogen isotope fractionation effects for kinetic and equilibrium processes have been reported to range from 1.33 to 1.50. Evaporative tritium enrichment is, therefore, 33% to 50% larger than that determined for deuterium. With this knowledge, the tritium activity measured in any sample of transpired water can be corrected to account for evaporative tritium fractionation in the plant leaf tissue.

For the Berkeley Laboratory samples, the first transpired water samples from *Eucalyptus globulus* and *Genista monspessulana* are enriched in deuterium by 22.1% and 35.2%, respectively. If mass dependent $^3H$ fractionation is assumed to be 50% stronger than $^2H$ fractionation, the tritium activities of the first collected samples require downward correction by 33.1% and 52.8%, respectively. Thus, for the plant species investigated at Berkeley Laboratory, the tritium activities in first-collected samples require only minor downward corrections of 3–5% to represent xylem water values and subsurface soil water or shallow groundwater values. Larger corrections may be required in arid regions where evaporative deuterium and tritium enrichments may be more pronounced or for plant species that contain a larger component of evaporated water in leafy tissue.

What is claimed is:

1. A method for determination of $^{18}O/^{16}O$ and $^2H/^1H$ ratios and $^3H$ concentrations of xylem and subsurface waters using time series sampling, insulating sampling chambers, and combined $^{18}O/^{16}O$, $^2H/^1H$, and $^3H$ concentration data on transpired water, said method comprising steps:

(a) collecting samples of transpired water from a plant;

(b) determining stable isotopic composition and tritium activities of plant transpired waters;

(c) plotting the stable isotopic compositions of transpired waters and a local Meteoric Water Line or Global Meteoric Water Line on a Cartesian graph of $\delta D$ vs $\delta^{18}O$;

(d) constructing a mixing line of best fit of the stable isotopic data of step (c);

(e) determining the stable isotopic compositions of xylem water or subsurface water from the point of intersection of the mixing line and the local or Global Meteoric Water Line and the amount of evaporative fractionation of $^2H$ and $^{18}O$ in transpired water samples; and (f) calculating the amount of evaporative tritium enrichment by inference from the amount of deuterium fractionation per transpired water sample and the well known mass dependence of light isotopic fractionation.

2. The method of claim 1 wherein the samples are collected by using insulating sampling chambers.

3. The method of claim 2 wherein insulating sampling chambers securely affixed to or around living plant tissues provide water saturated conditions within the chamber and preclude evaporation of collected transpired water to the atmosphere.

4. The method of claim 3 wherein the insulating sampling chambers enhance water transpiration from the plant tissue.

5. The method of claim 4 wherein the samples are collected by using time series sampling.

6. The method of claim 5 wherein water is collected and removed daily in predetermined intervals for periods of time from about several hours to about several days.

7. The method of claim 6 wherein time-series sampling produces transpired water samples with differing proportions of xylem water and leaf water.

8. The method of claim 7 wherein the time-series sampling is used for construction of a mixing line on a $\delta D$ vs $\delta^{18}O$ diagram.

9. The method of claim 8 wherein the step (f) further involves the arithmetic determination of the amount of evaporative tritium enrichment in transpired water samples.

10. The method of claim 9 wherein step (f) further comprises the correction of measured tritium concentrations or activities to reflect those of the plant xylem water, or isotopically equivalent shallow subsurface waters used by the plant prior to evaporation.

11. The method of claim 10 wherein the measured isotopic data of oxygen isotopes $^{18}O/^{16}O$ ratio and hydrogen isotopes $^{2}H/^{1}H$ ratio and $^{3}H$ concentrations express the evaporative isotopic fractionation in the leafy material of the plant.

12. The method of claim 11 wherein the stable isotopic compositions and tritium concentrations are determined in plant xylem waters or shallow subsurface waters in the environment.

13. The method of claim 12 useful for water management, land use planning, public health, radiological, hydrologic, engineering, ecological, forensic, agricultural, biological, or botanical monitoring investigations.

14. A method for determining the amount of evaporative enrichment in $^{18}O$, $^{2}H$, and $^{3}H$ in transpired waters, said method comprising steps:
  (a) collecting samples of transpired water from a plant, soil waters or shallow groundwaters daily;
  (b) determining stable isotopic data and tritium activities of plant transpired waters;
  (c) plotting the stable isotopic compositions of transpired waters and a local Meteoric Water Line or Global Meteoric Water Line on a Cartesian graph of $\delta D$ vs $\delta^{18}O$;
  (d) constructing a mixing line of best fit of the stable isotopic data of step (c);
  (e) determining the stable isotopic composition of xylem water or subsurface water from the point of intersection of the mixing line and the local or Global Meteoric Water Line and the amount of evaporative fractionation of $^{2}H$ and $^{18}O$ in transpired water samples; and
  (f) calculating the amount of evaporative tritium enrichment by inference from the amount of deuterium fractionation per transpired water sample and the well known mass dependence of light isotopic fractionation.

* * * * *